United States Patent
Grant et al.

[19]

[11] Patent Number: 6,030,337
[45] Date of Patent: Feb. 29, 2000

[54] CONTINENCE AUGMENTOR AND METHODS FOR URINARY CONTROL

[75] Inventors: Robert C. Grant, New Hope; Sidney F. Hauschild, St. Paul; Mark Polyak, Minnetonka, all of Minn.

[73] Assignee: American Medical Systems, Inc., Minnetonka, Minn.

[21] Appl. No.: 09/126,670

[22] Filed: Jul. 30, 1998

[51] Int. Cl.⁷ ...................................................... A61N 5/00
[52] U.S. Cl. ................... 600/29; 128/885; 128/DIG. 25; 600/30
[58] Field of Search ................... 128/DIG. 25, 884–885; 600/29–33; 623/11–12

[56] References Cited

U.S. PATENT DOCUMENTS

| | | |
|---|---|---|
| 2,510,766 | 6/1950 | Surface . |
| 3,547,401 | 12/1970 | Gurnee et al. . |
| 3,758,073 | 9/1973 | Schulte . |
| 3,841,304 | 10/1974 | Jones . |
| 4,210,132 | 7/1980 | Perlin . |
| 4,587,954 | 5/1986 | Haber . |
| 4,631,062 | 12/1986 | Lassen et al. . |

(List continued on next page.)

FOREIGN PATENT DOCUMENTS

| | | |
|---|---|---|
| 0535778 B1 | 7/1995 | European Pat. Off. . |
| 0780105 A2 | 6/1997 | European Pat. Off. . |
| 92/06731 | 4/1992 | WIPO . |
| 92/11826 | 7/1992 | WIPO . |
| 92/19192 | 11/1992 | WIPO . |
| 93/08765 | 5/1993 | WIPO . |

(List continued on next page.)

*Primary Examiner*—Cary O'Connor
*Assistant Examiner*—Michael Astorino
*Attorney, Agent, or Firm*—Oppenheimer Wolff & Donelly, LLP

[57] ABSTRACT

A female continence augmentor stops involuntary urine loss due to transient increases in bladder pressure but allows urine flow when automatically opened by transmitted bladder pressure during voluntary voiding. The augmentor improves coaptation and increases midurethral resistance to opening with a resilient mount releasably adhered adhesively to the body in position to prevent inadvertent urine loss. An intralumenal part on the mount has a resilient portion extending into the urethra for urging the dorsal midurethral wall in a dorsal direction for stretching and/or reshaping the midurethral lumen to an arc. The portion has a member located to engage the midurethral wall. A coaptation improver on the member engages with the adjacent midurethra. The improver carries biocompatible hydrophilic material adapted to coact with mucus and mucosa within the urethra. A coated biocompatible hydrophilic membrane can be the member with opposed generally rectangular major surfaces and is circumscribed by an edge. The hydrophilic membrane is bowed along the edge transverse between sides thereof for bearing against the inside of the midurethral walls. The membrane has a mesh of flexible polymer and an arc shape between the sides so the opposed major surfaces are concave and convex. Two struts can extend from the sides to the portion. A method of making the augmentor has the steps of forming the mount of resilient material. The resilient material adheres to the body to support the augmentor in position to prevent inadvertent urine loss through the midurethral lumen. The part on the mount extends into the urethra. Connecting the part to the mount and locating the member on the portion for placement relative to the mount intralumenally is a step. The method step of forming includes molding the mount of a polymer. The step of locating the member uses at least one or two struts. The method has the step of adding an adhesive to the mount and increasing coaptation of the portion with a material. A method of using the augmentor has the steps of inserting the part into the urethra so that the member is within the midurethral lumen and placing the mount adjacent to the urethral exit to retain the member therein. Applying resistance inside the urethra with the member by the portion is a step of using. Urging the dorsal midurethral wall in a dorsal direction and engaging the urethral wall, especially the midurethral wall to remove laxity therein are steps of using.

20 Claims, 10 Drawing Sheets

U.S. PATENT DOCUMENTS

| | | |
|---|---|---|
| 4,690,677 | 9/1987 | Erb . |
| 4,822,333 | 4/1989 | Lavarenne . |
| 4,968,294 | 11/1990 | Salama . |
| 5,074,855 | 12/1991 | Rosenbluth et al. . |
| 5,082,006 | 1/1992 | Jonasson . |
| 5,114,398 | 5/1992 | Trick et al. . |
| 5,140,999 | 8/1992 | Ardito . |
| 5,336,208 | 8/1994 | Rosenbluth et al. . |
| 5,352,182 | 10/1994 | Kalb et al. . |
| 5,483,976 | 1/1996 | McLaughlin et al. . |
| 5,640,976 | 6/1997 | Levius . |
| 5,662,582 | 9/1997 | Levius et al. . |
| 5,711,314 | 1/1998 | Ardito . |
| 5,722,931 | 3/1998 | Heaven . |
| 5,755,236 | 5/1998 | Dann et al. . |
| 5,813,974 | 9/1998 | Dolade Guardia . |

FOREIGN PATENT DOCUMENTS

| | | | |
|---|---|---|---|
| 94/26915 | 11/1994 | WIPO . | |
| 96/26688 | 9/1996 | WIPO . | |
| 96/39096 | 12/1996 | WIPO . | |
| 96399989 | 12/1996 | WIPO | A61F 2/00 |
| 96399990 | 12/1996 | WIPO | A61F 2/00 |
| 96399991 | 12/1996 | WIPO | A61F 2/00 |
| 97/06758 | 2/1997 | WIPO . | |
| 97/17909 | 5/1997 | WIPO . | |
| 97/25947 | 7/1997 | WIPO . | |
| 98/19640 | 5/1998 | WIPO . | |
| 98/2555 | 6/1998 | WIPO . | |

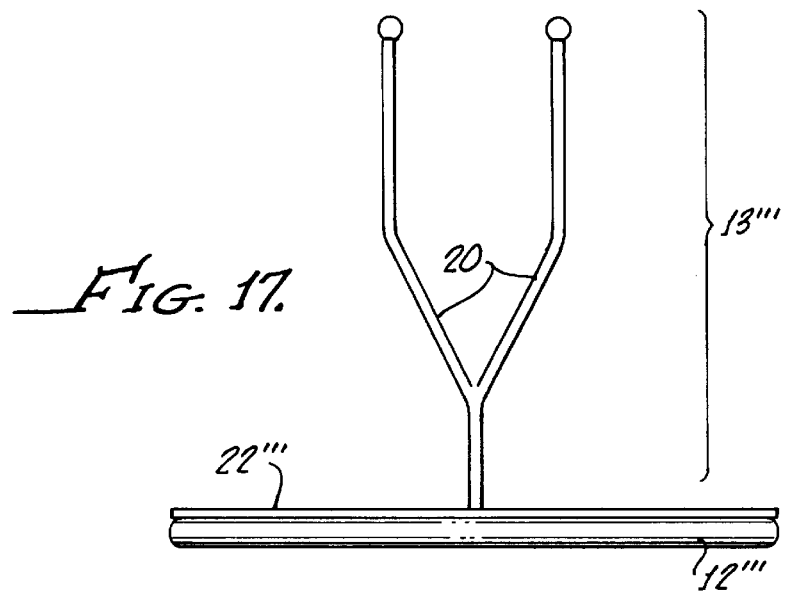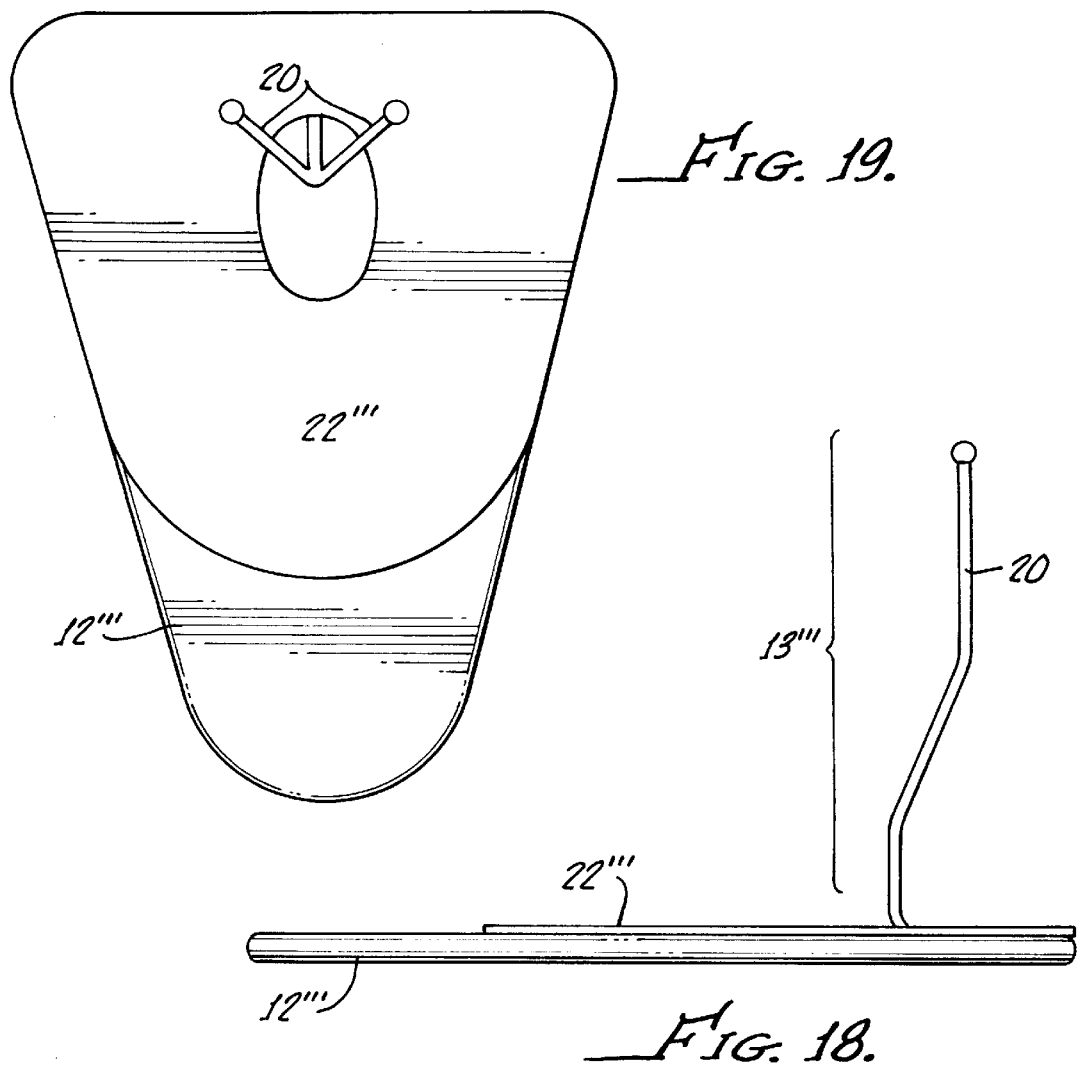

CONTINENCE AUGMENTOR AND METHODS FOR URINARY CONTROL

FIELD OF INVENTION

This invention relates to a female continence augmentor for alleviating urinary incontinence. More particularly, the invention is concerned with a patient controlled female continence augmentor which prevents undesirable involuntary urine loss while allowing relief when needed without removal of the female continence augmentor from the body of the patient. A most preferred embodiment of the female continence augmentor is for alleviating urinary incontinence, particularly stress incontinence, in a female patient.

BACKGROUND OF THE INVENTION

Urinary incontinence, which is a condition involving involuntary loss of urine, is a problem with millions of people. It is much more prevalent among women than men. In some patients, loss of urine is associated with transient increases in intra-abdominal pressure that result from activities such as coughing, sneezing, lifting, straining, exercise and in severe cases, even simply changing body position. This is called stress incontinence.

The normal urinary continence mechanism combines contributions from several components including muscles in and around the urethra, blood pressure in the urethral vascular plexus between the smooth muscle in the urethral wall and the epithelial lining, the mucosal seal between the walls of the closed urethral lumen (coaptation), and support from endopelvic fascia. During urination the muscles in and around the urethra relax and the bladder muscle (the detrusor) contracts. Fluid pressure from the bladder overcomes the mucosal seal, the lumen opens and urine is expelled.

While the bladder is filling, increases in bladder pressure normally induce reflex reactions in the muscles of the continence system to increase urethral closure pressure. This reflex response is normally adequate to prevent involuntary urine loss. If the resistance to urethral opening is insufficient to keep the lumen sealed, the female patient experiences episodes of stress incontinence. Stress incontinence results from inadequate functioning of one or more of the components of the normal continence system.

Options currently available for management of female urinary stress incontinence include the use of externally applied absorbent products, pelvic muscle exercises, electrical stimulation of pelvic muscles, devices that occlude the urethra either internally or externally at the urethral meatus, and injections that add bulk to the urethral wall and surgery. A number of external and internal female continence devices have been patented.

U.S. Pat. No. 5,074,855 discloses a device for controlling urinary incontinence in a human female including a resilient pad configured to seal against and occlude the urethral meatus of the user. A similar device is disclosed in U.S. Pat. No. 5,336,208. In those devices, an adhesive is provided to seal the body of the device against the urethral meatus.

International Applications No. 96/39989, 96/39990 and 96/39991 each disclose a female urinary incontinence device in the form of an urethral cap with a partially deformable body portion, a hand gripping portion and a body contacting surface. The body portion defines a chamber which allows for a vacuum seal when applied to the patient's body.

U.S. Pat. No. 5,082,006 has a shaft to be inserted into the urethra and one or more knobs on the shaft to plug the passage of urine therethrough. A flap on the proximal end of the shaft holds the positioning of the shaft in the urethra.

Each of the above devices prevents urinary loss by occluding the internal or external urethral orifice and each has to be removed by the patient to allow micturition.

It is desirable to have a device which satisfactorily prevents urinary loss and also permits voluntary voiding without needing to remove the device from the body of the patient. It has now been found that these benefits may be achieved with a female continence augmentor that prevents involuntary urine loss while allowing urine flow during voluntary micturition. The female continence augmentor, described herein, achieves the desired effects by gently stretching and reshaping the midurethra from within its lumen. Stretching the perimeter of the lumen increases tension in the surrounding midurethral wall bringing the opposing surfaces of the epithelial lining into more intimate contact for enhancing coaptation. Coupled with the action of the regular continence mechanism, the increased tension and improved coaptation make the urethra more resistant to dilation by urine during transient increases in abdominal pressure, thus relieving stress incontinence.

When the user of the female continence augmentor wishes to void, the muscles of her continence mechanism relax, reducing tension in the urethral wall sufficiently to permit dilation of the lumen under normal bladder pressure. The female continence augmentor acts as a spring, exerting force directly proportional to the compressive force applied by the muscles of the continence mechanism. When the continence mechanism relaxes, the force from the augmentor drops to a level that does not significantly increase the fluid pressure required to dilate the urethra for urination. The female continence augmentor maintains contact with the dorsal midurethral wall at all times, but the reduced muscular tension allows urine pressure to stretch the urethra, opening a slit-shaped passage for urine between the ventral urethral wall and the ventral surface of the augmentor.

When voiding is complete, contraction of the sphincteric muscles restores tension in the urethral wall and the female continence augmentor resumes functioning automatically. Thus, the female continence augmentor functions through dynamic interactions with the biological continence mechanism. Its mode of action is clearly different than that of previous intraurethral continence devices, which act as plugs that must be removed or plugs with valves that must be externally activated for voiding.

SUMMARY OF THE INVENTION

The female continence augmentor adapted to prevent involuntary urine loss due to transient increases in bladder pressure but to passively allow urine flow during voluntary emptying of the bladder. The female continence augmentor improves urethral coaptation and increases mid-urethral resistance to opening the lumen while the bladder is filling. The female continence augmentor preferably has a mount formed of a resilient material. The mount most preferably adheres to the female body about the urethral exit to support the female continence augmentor in position to prevent inadvertent urine loss through the midurethral lumen. The mount may perhaps include a layer of adhesive applied thereto and the adhesive might be adapted to releasably attach to the female body.

An intralumenal part may be carried on the mount. The intralumenal part preferably includes a resilient portion carried on the mount. The resilient portion can extend into the urethra and could be adapted to at least urge the dorsal midurethral wall in a dorsal direction to stretch and/or reshape the midurethral lumen to have a more arcuate shape transversely thereacross. Thus the midurethral lumen in cross section would preferably exhibit a crescent shape of smaller radius. The intralumenal part might include two struts or a member attached to one or two struts extending from the resilient portion for stretching, reshaping and repositioning the midurethral lumen intralumenally.

The member might be adapted for engaging the urethral wall, especially the midurethral wall to remove laxity therein and for enhancing coaptation and increasing urethral resistance to opening. The patient may void voluntarily with normal muscle control but otherwise without requiring conscious action to operate the female continence augmentor or needing to remove, activate, inactivate, or alter it. Following voiding, the continence augmentation function resumes automatically by removing laxity in the midurethral lumen.

The member could include a coaptation improver located thereon and in position for and adapted for engagement with the adjacent midurethral walls. It is preferred that the coaptation improver be biocompatible hydrophilic material adapted to coact with mucus and mucosa within the urethra to prevent involuntary urine loss. The member may be or include a flexible membrane of polymeric material. The flexible membrane might have a structural shape of opposed major surfaces with interstices thereacross. The opposed major surfaces are preferably surrounded by an edge and are preferably generally rectangular.

The member is supported by one or two struts which extend from the resilient portion to the member to urge it against the wall of the midurethral lumen. The two struts may preferably spread apart relative to each other so that the two struts are closer to one another at the resilient portion than at the sides of the member.

The member or flexible membrane might be coated across at least its opposed major surfaces with the biocompatible hydrophilic material that cooperatively fills any gaps between the midurethral walls and the member or flexible membrane. The biocompatible hydrophilic material may promote adherence therewithin and therebetween to seal and prevent involuntary urine loss thereacross. The member or flexible membrane is preferably bowed along the edge transverse to its sides for forming a resilient structure bearing against the midurethral walls. The flexible membrane may be formed of a mesh preferably of flexible polymer. The flexible membrane could possibly have an arcuate shape between opposite sides thereof wherein the opposed major surfaces might perhaps be concave and convex generally in accord with the contour of midurethral lumen cross section.

A method of making the female continence augmentor preferably may improve urethral coaptation and increase mid-urethral resistance to opening the lumen. The method of making preferably has the steps of forming the mount of resilient material and perhaps including the intra lumenal part carried on the mount for extending into the urethra and adapted to at least urge the dorsal midurethral wall in a dorsal direction to stretch and/or reshape the midurethral lumen to have a more arcuate shape transversely thereacross to exhibit a smaller radius. The intralumenal part might include a member attached to the resilient portion for stretching, reshaping and repositioning the midurethral lumen intralumenally for at least urging the dorsal midurethral wall in a dorsal direction for stretching and/or reshaping the midurethral lumen to be a more arcuate shape transversely thereacross. The method of making may have the steps of connecting the intralumenal part to the mount and locating one or more struts on the resilient portion in position for placement relative to the mount intralumenally. The method of making could include the step of forming by molding the mount of a polymer material. The method of making might have the step of locating the member on one or more struts connected to the resilient portion. Substituting the flexible membrane between two struts may be a step. The method of making preferably has the steps of adding adhesive to the mount and having biocompatible hydrophilic material on the member or the flexible membrane to increase coaptation.

A method of using the female continence augmentor might have the mount connected to an intralumenal part. The method of using preferably may include the steps of inserting the intralumenal part into the urethra so that the struts or member thereon are within the midurethral lumen. The step of placing the mount adjacent to the urethral exit to retain the struts or the member in the midurethral lumen can be performed. Stretching and/or reshaping the inside of the urethra with the struts or member urged by the resilient portion that is preferably connected between the mount and struts might be a step. The method of using may include steps of urging the dorsal midurethral wall in a dorsal direction for stretching and/or reshaping the midurethral lumen to have a more arcuate shape transversely thereacross and engaging the urethral wall, especially the midurethral wall to remove laxity therein and for enhancing coaptation and increasing urethral resistance to opening. The patient may void voluntarily without requiring conscious action to operate the female continence augmentor. That is, there is no need to remove, activate, inactivate or alter it. Following voiding, the female continence augmentor resumes functioning automatically.

BRIEF DESCRIPTION OF THE DRAWINGS

FIG. 17 is a front view of the alternate female continence augmentor of FIG. 15.

FIG. 18 is a side view shown as an elevation of the alternate female continence augmentor.

FIG. 19 is top plan view of the alternate female continence augmentor of FIG. 15.

DETAILED DESCRIPTION OF THE DRAWINGS

Figure 1:
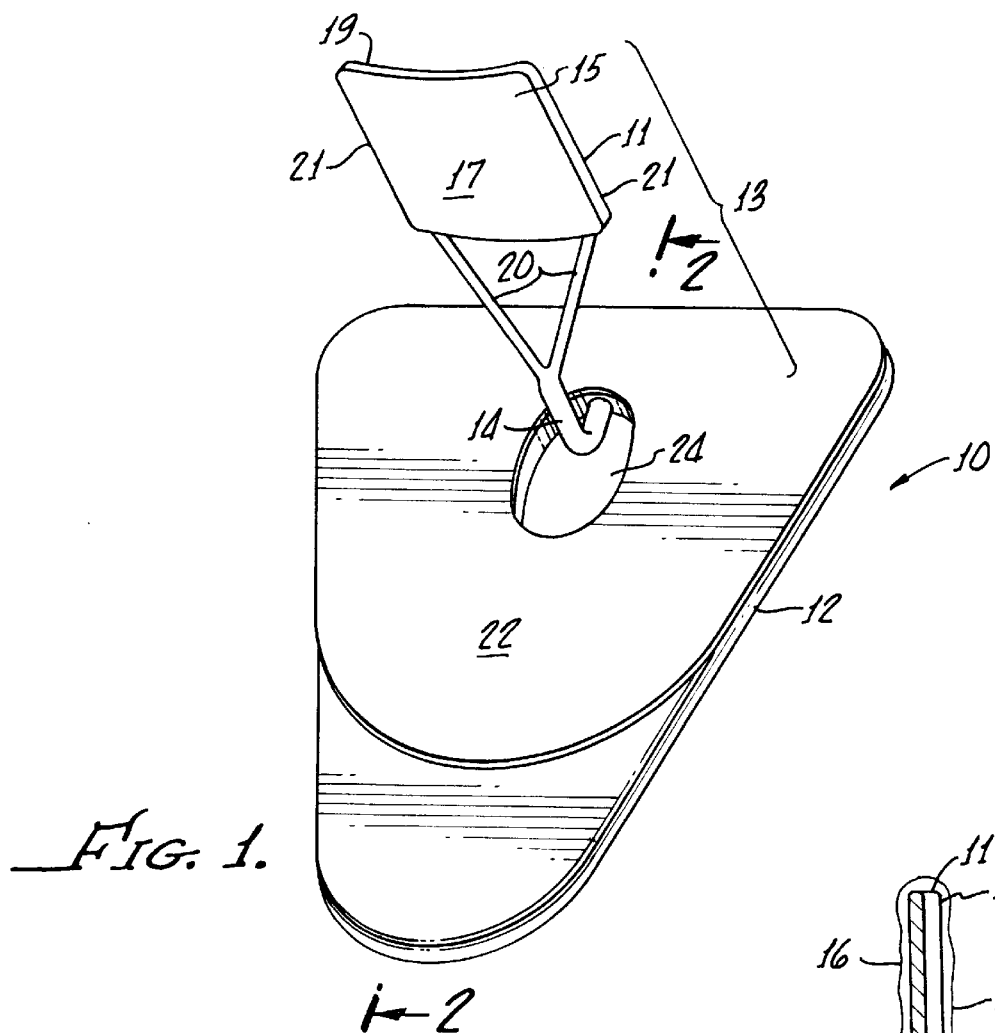
FIG. 1 is a view in perspective of a female continence augmentor adapted to prevent involuntary urine loss due to transient increases in bladder pressure but to passively allow urine flow during voluntary emptying of the bladder.
Figure 2:
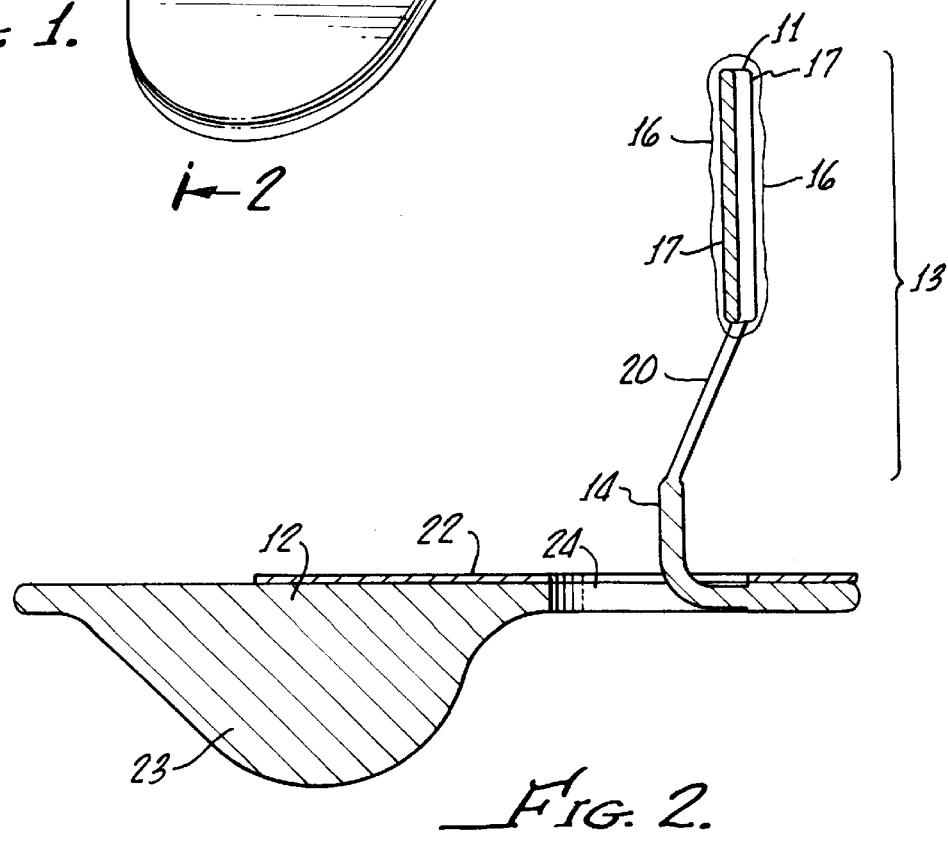
FIG. 2 is a plan view in cross section of the female continence augmentor as would be seen along line 2—2 of FIG. 1.

Several slightly differing female continence augmentors 10, 10', 10", or 10''' are shown in similar perspective views in the FIGS. 1, 7, 11 and 15, respectively. The reference numbers in each group of Figures for each of the four embodiments disclosed will include identical reference numbers for similar components but for clarity prime numbers will distinguish each of the various embodiments. The female continence augmentor 10, 10', 10" or 10''' is adapted for insertion into a female's midurethral lumen and some have in FIGS. 1, 7, and 11, a flexible membrane 11, 11' or 11" formed of a flexible material. The flexible membrane 11, 11' or 11" may be a formed member 15, 15' or 15" and/or might be assembled from separately made parts. The flexible membrane 11, 11' or 11" is preferably made from a variety of polymer materials that impart the following key characteristics: stability, biocompatability, limited water absorption, very easy and reversible distensibility and compressibility, receptivity to bonding with a surface coating of mucoadhesive. Suitable membranes with these characteristics may be produced from a variety of known polymer materials using molding, casting, extruding, braiding, weaving, knitting or other manufacturing methods that yield the desired characteristics with the polymer selected.

Laxity or slack in the female urethra decreases the resistance of the urethral wall to opening by pressurized urine. This problem is alleviated by the disclosed female continence augmentor 10, 10', 10" or 10'''. The female continence augmentor 10, 10', 10" or 10''' is adapted to prevent involuntary urine loss due to transient or unintended increases in bladder pressure but to passively allow urine flow during voluntary or intended emptying of the bladder. The female continence augmentor 10, 10', 10" or 10''' increases midurethral resistance to opening the urethral lumen and improves urethral coaptation. All the female continence augmentors 10, 10', 10" or 10''' have a mount 12, 12', 12" or 12''' formed of a resilient material to accommodate the contours of the female anatomy. The mount 12, 12', 12" or 12''' adheres to the female body about the urethral exit to support the female continence augmentor 10, 10', 10" or 10''' in position to prevent, as explained herein, inadvertent urine loss through the midurethral lumen.

An intralumenal part 13, 13', 13" or 13''' is respectively, carried on the mount 12, 12', 12" or 12''' and is shaped for extending up into the urethra from the mount 12, 12', 12" or 12'''. The mount 12, 12' 12" or 12''' adheres about but does not block the urethral exit. The intralumenal part 13, 13', 13" or 13''' also does not block the urethral exit or the urethra connected thereto. The intralumenal part 13, 13', 13" or 13''' includes resilient portion 14, 14', 14" or 14''' extending from the mount 12, 12', 12" or 12''' as best seen in FIGS. 1, 7, 11 or 15 respectively. Thus the resilient portion 14, 14', 14" or 14''' can extend into the urethra in position for at least urging the dorsal midurethral wall in a dorsal direction for stretching and/or reshaping the midurethral lumen to have a more arcuate shape transversely thereacross. That is to say that the resilient portion 14, 14', 14" or 14''' pushes the inside dorsal or back wall of the urethra toward the vagina.

Figure 7:
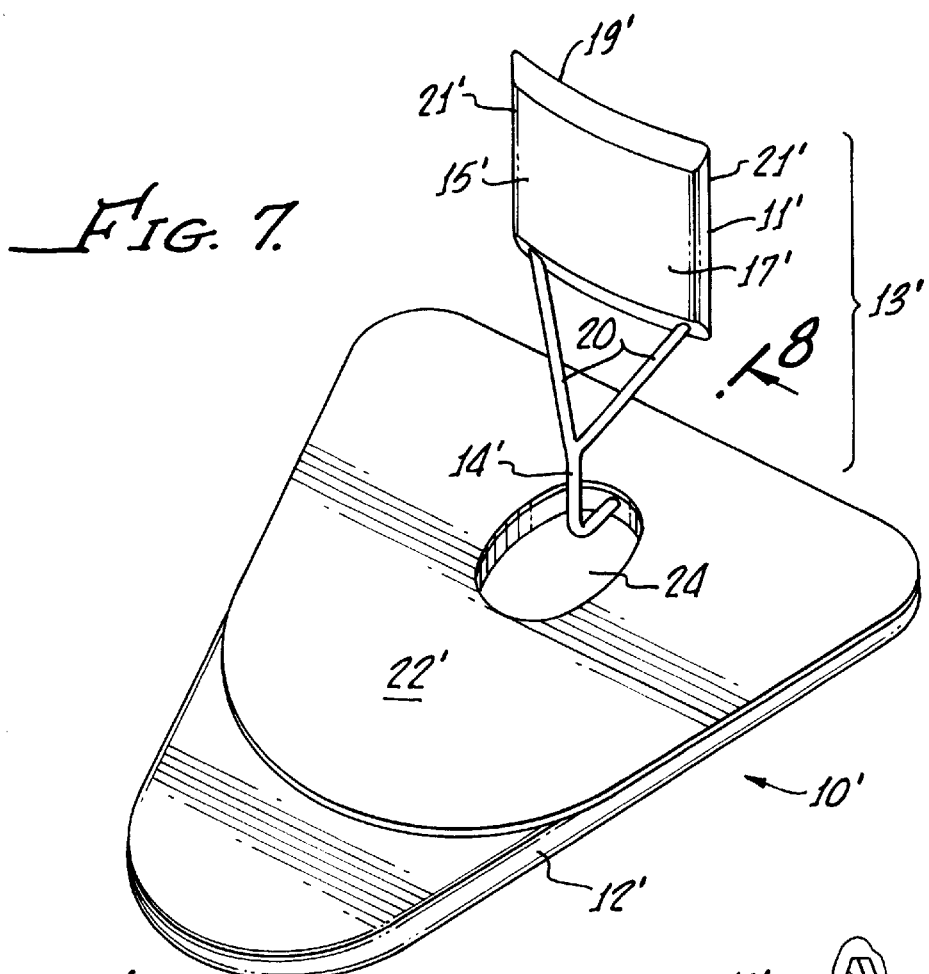
FIG. 7 is a top view in perspective of an alternative female continence augmentor adapted to prevent involuntary urine loss due to transient increases in bladder pressure but to passively allow urine flow during voluntary emptying of the bladder.
Figure 8:
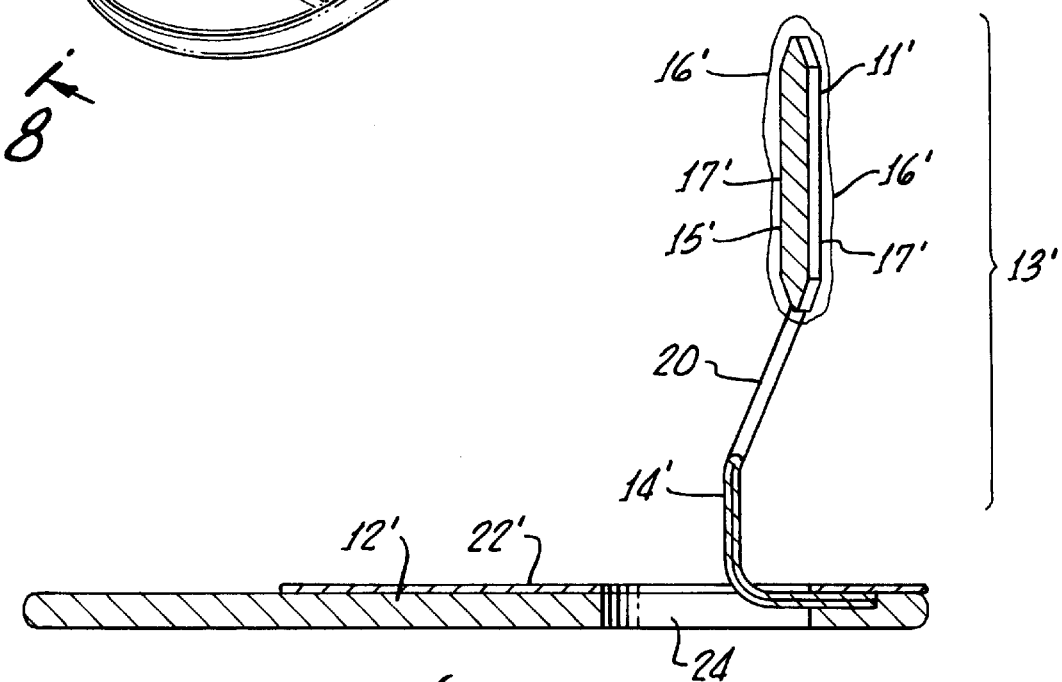
FIG. 8 is a plan view in cross section of the alternative female continence augmentor as would be seen along line 8—8 of FIG. 7.
Figure 9:
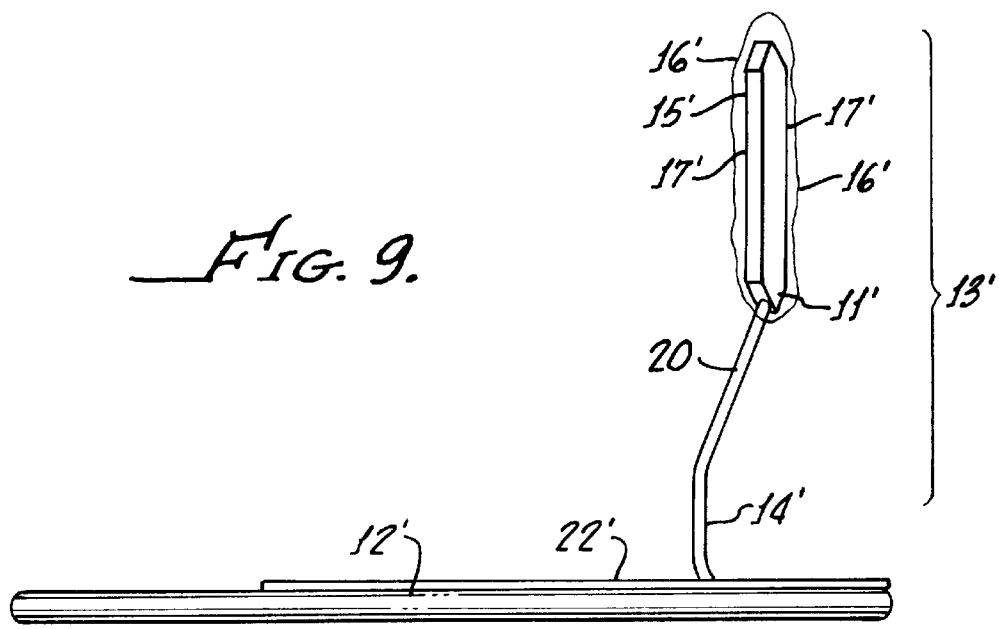
FIG. 9 is a side view shown as an elevation of the alternative female continence augmentor of FIG. 7.
Figure 10:
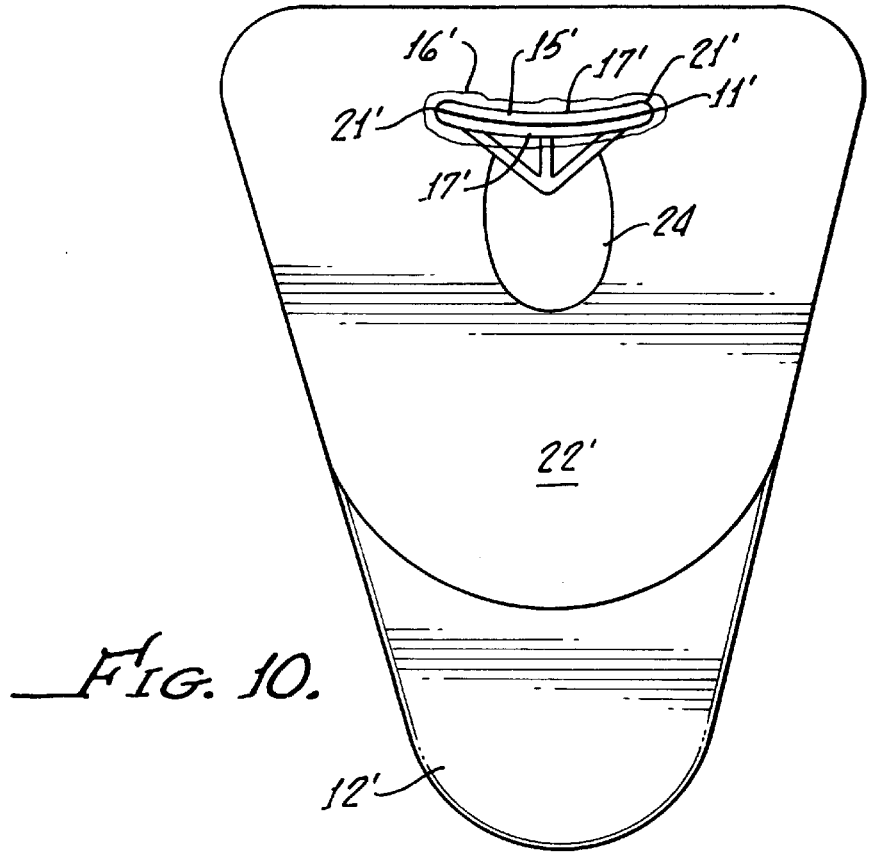
FIG. 10 is an enlarged top plan view of the alternative female continence augmentor of FIG. 7.
Figure 11:
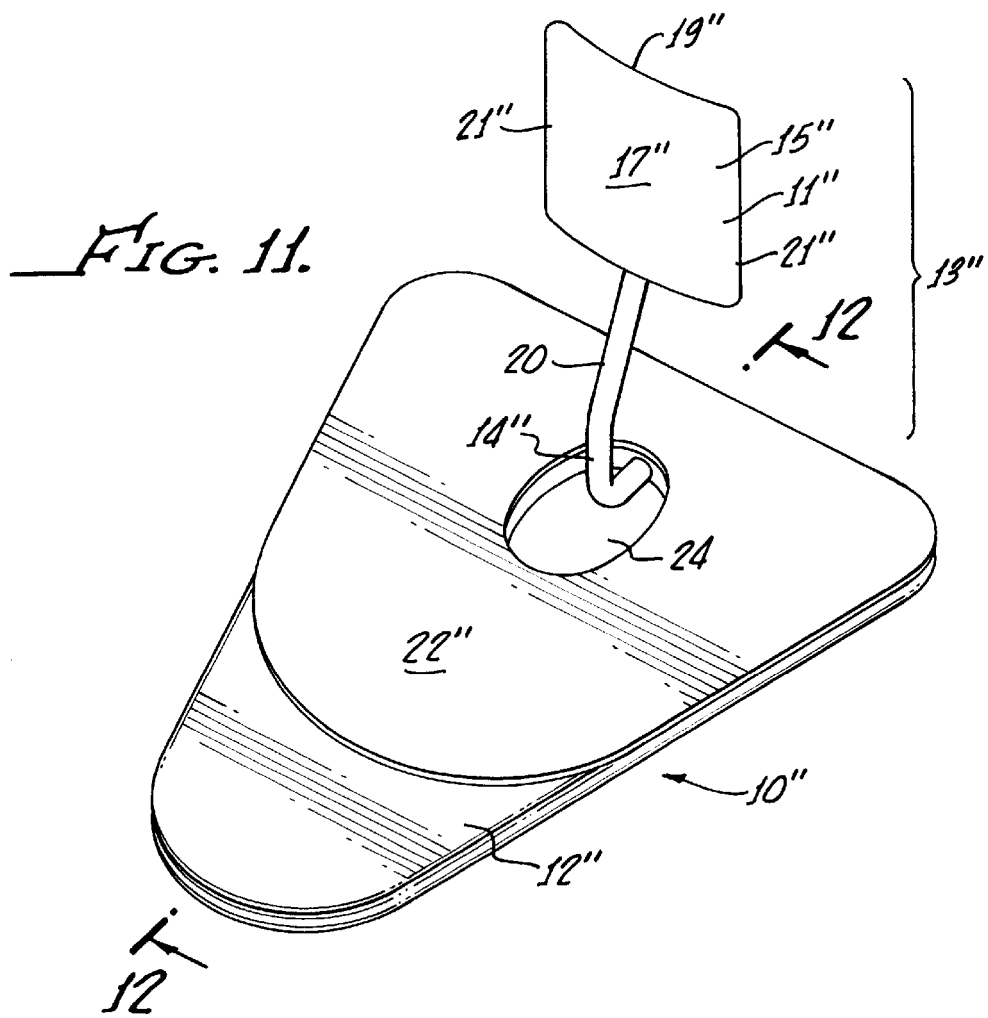
FIG. 11 is a view in perspective of an optional female continence augmentor adapted to prevent involuntary urine loss due to transient increases in bladder pressure but to passively allow urine flow during voluntary emptying of the bladder.
Figure 12:
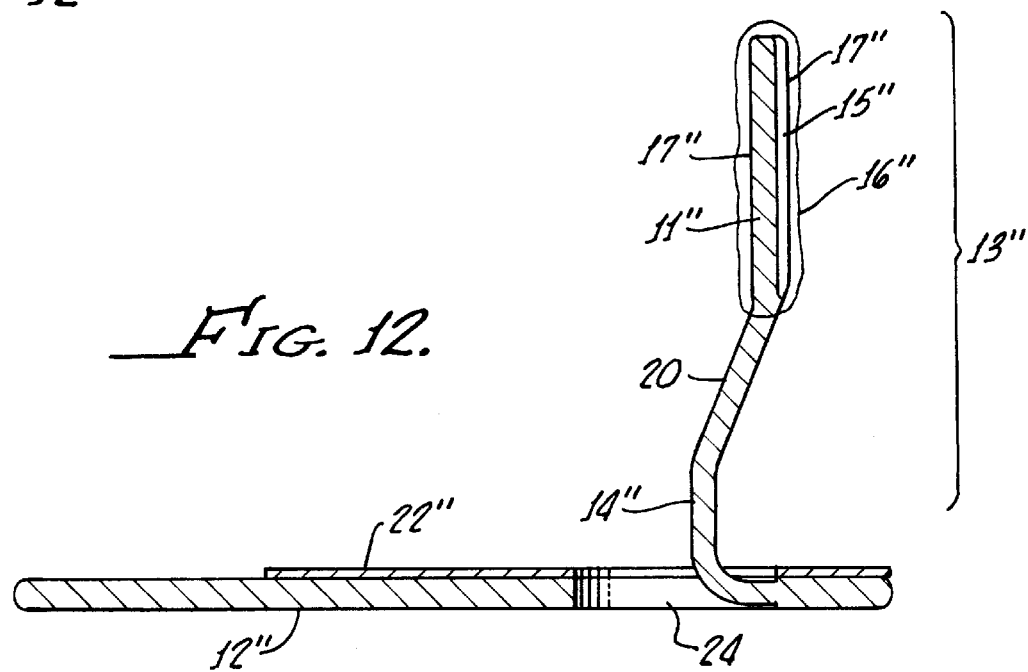
FIG. 12 is a plan view in cross section of the optional female continence augmentor as would be seen along line 12—12 of FIG. 11.
Figure 13:
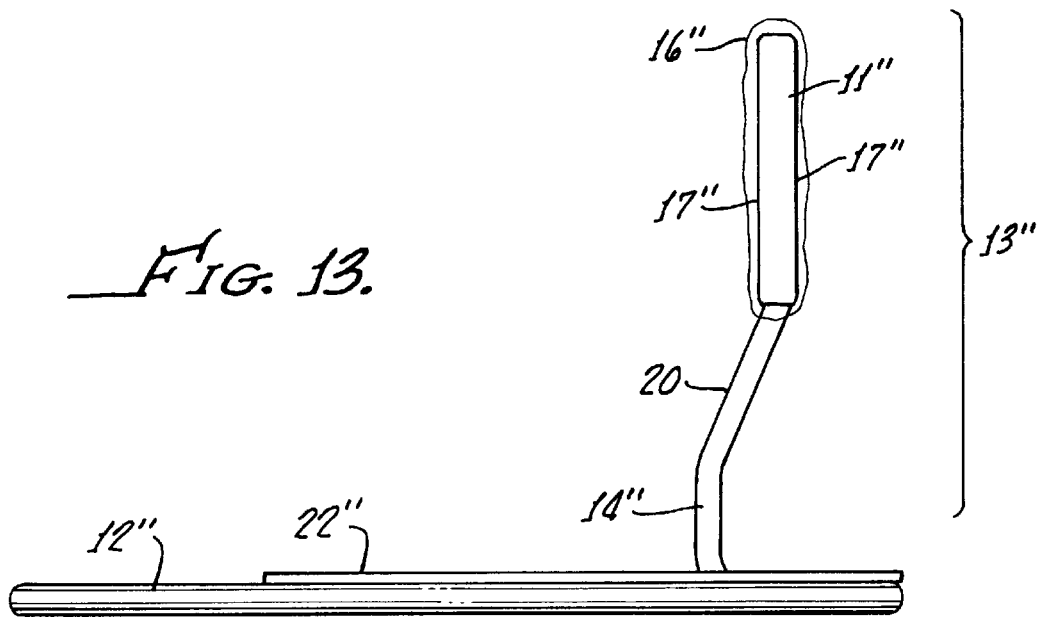
FIG. 13 is a side view shown as an elevation of the optional female continence augmentor of FIG. 11.
Figure 14:
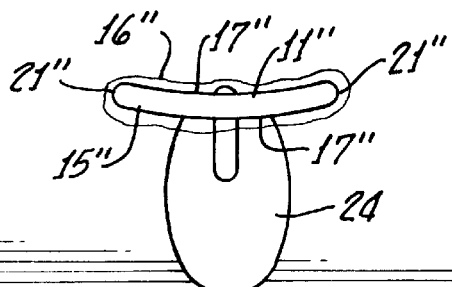
FIG. 14 is top plan view of the optional female continence augmentor of FIG. 11.

The intralumenal part 13, 13' or 13" in FIGS. 1, 7 and 11 includes the member 15, 15' or 15" attached to the resilient portion 14, 14' or 14" for positioning intralumenally in the midurethral lumen. Thus the resilient portion 14, 14' or 14" carries its respective member 15, 15' or 15" in the urethra located for engaging the urethral wall, particularly the midurethral wall to remove laxity therein and for enhancing coaptation and increasing urethral resistance to opening. The patient may void voluntarily without requiring conscious action to operate the female continence augmentor 10, 10', 10" or 10''' or needing to remove, activate, inactivate, or alter it. Bladder pressure will, during voiding, expand the urethra permitting urine to pass the female continence augmentor 10, 10', 10" or 10'''. When voiding is completed the continence augmentation function resumes automatically.

The flexible membrane 11,11', or 11" or the member 15,15' or 15" may be coated with a coaptation improver 16, 16' or 16", see FIGS. 1 to 14, located on flexible membrane 11, 11', or 11" or the member 15, 15' or 15" in a position for and adapted for engagement with the adjacent midurethral walls. It is preferred that, the coaptation improver 16, 16' or 16" carry biocompatible hydrophilic material, such as mucopolysaccharides, mucoadhesives, dextrans, fruit pectins, polyethers, polyacrylate and its derivatives, polyacrylonitrile and its derivatives, homopolysaccharides, heteropolysacchrides and their derivatives. The biocompatible hydrophilic material coaptation improver 16, 16' or 16" is adapted to coact with mucus and mucosa within the urethra to prevent involuntary urine loss. The flexible membrane 11, 11' or 11" may be coated across at least its opposed major surfaces 17,17' or 17" with the biocompatible hydrophilic material coaptation improver 16, 16' or 16" that cooperatively fills any space between the midurethral walls and the flexible membrane 11, 11' or 11" or the member 15, 15' or 15" to promote adherence therebetween to seal and prevent involuntary urine loss thereacross.

The formed member 15, 15' or 15" might be made as the flexible membrane 11,11' or 11" having a length and thickness of about 12 to 15 mm by 0.5 to 1.0 mm. The flexible membrane 11, 11' or 11" or the member 15,15' or 15" has opposed major surfaces 17,17' or 17" and perhaps with interstices 18 thereacross as shown only in FIG. 3, for example; although, any of the iterations may have interstices 18. The opposed major surfaces 17, 17' or 17" are surrounded by an edge 19, 19', or 19". The opposed major surfaces 17, 17' or 17" are preferably generally rectangular in shape but arcuate and as such are suitable for the midurethral lumen. The edge 19, 19' or 19" may be beveled, as shown in FIGS. 7 to 10, to enhance the continuity of coaptation along the upper and lower edges of the flexible membrane 11, 11' or 11" or member 15, 15' or 15".

Figure 15:
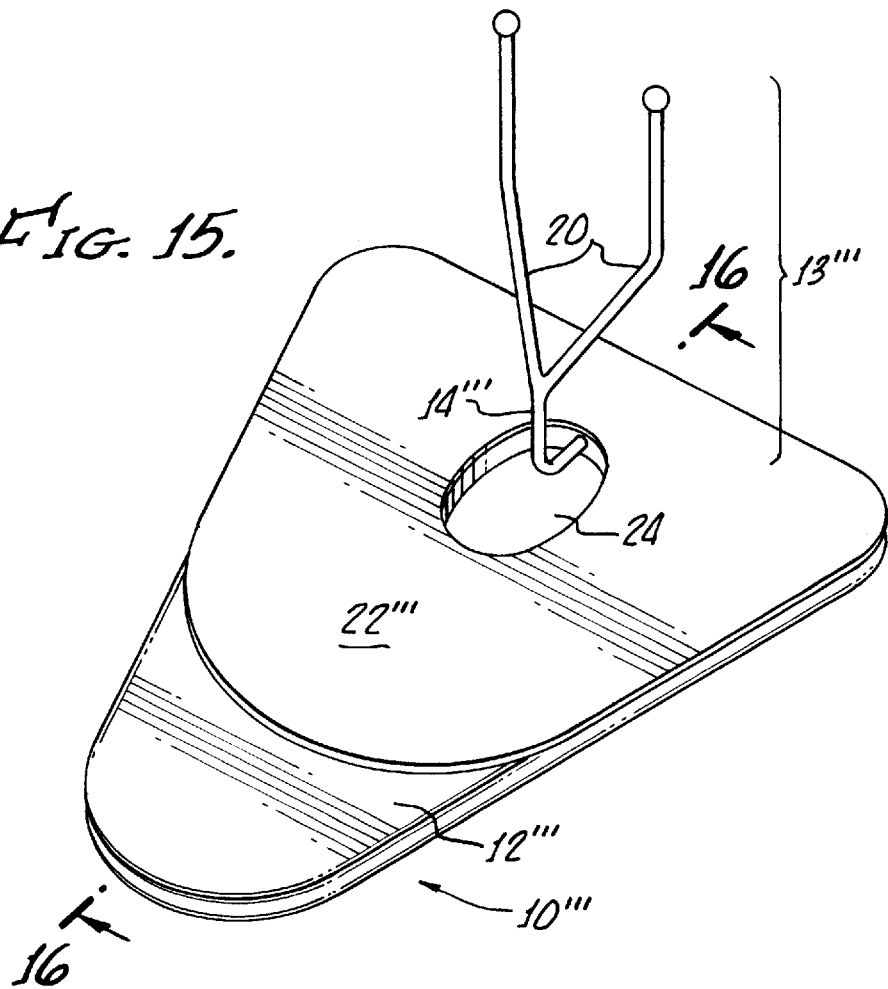
FIG. 15 is a view in perspective of an alternate female continence augmentor adapted to prevent involuntary urine loss due to transient increases in bladder pressure but to passively allow urine flow during voluntary emptying of the bladder.
Figure 16:
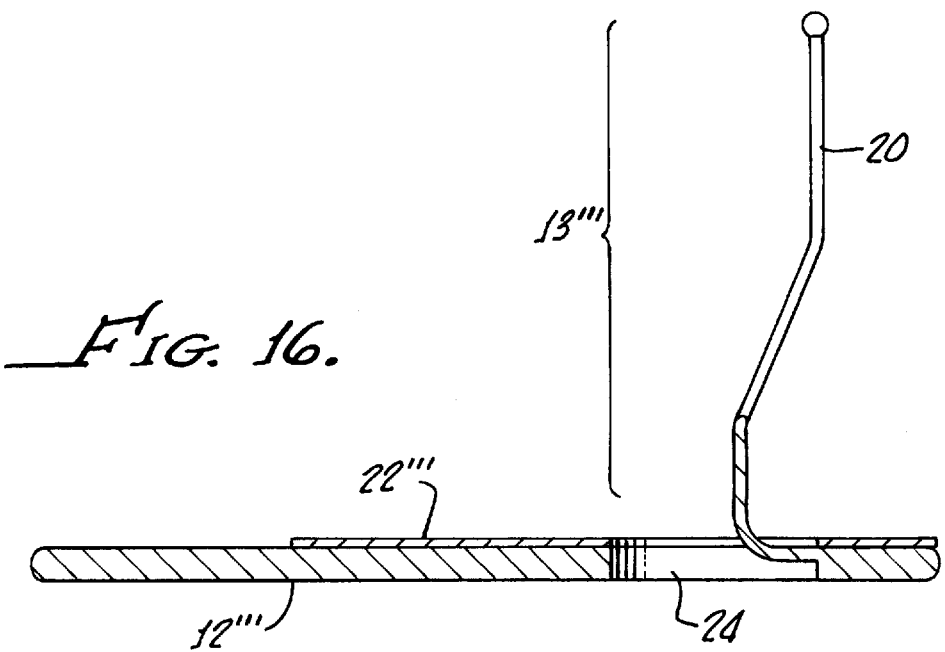
FIG. 16 is a plan view in cross section of the alternate female continence augmentor as would be seen along line 16—16 of FIG. 15.

One or two struts 20 extend from the resilient portion 14, 14' or 14" to the flexible membrane 11, 11' or 11" or member 15, 15' to urge the the flexible membrane 11,11' or 11" or member 15,15' or against the walls of the midurethral lumen to remove laxity. When two struts 20 are used they extend from opposite sides 21, 21' or 21" of the edge 19,19' or 19" of the flexible membrane 11, 11' or 11" or member 15, 15' or 15" to resilient portion 14, 14' or 14", see FIGS. 3, 7 and 11. When two struts 20 are used they may spread apart relative to each other so the two struts 20 are closer to one another at the resilient portion 14,14', 14" or 14"' than at the sides 21,21' or 21". In FIG. 15 the resilient portion 14"' has two struts 20 without any member or flexible membrane therebetween. The simplicity of this arrangement may make it the most preferred embodiment. That resilient portion 14"' has merely two struts 20 spaced apart to spread the midurethral lumen and remove laxity.

Figure 3:
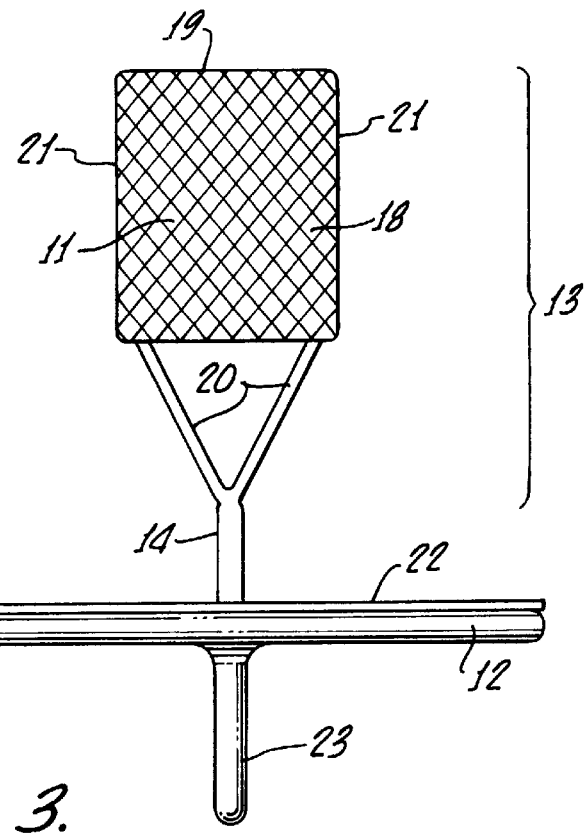
FIG. 3 is a front view of the female continence augmentor of FIG. 1.
Figure 4:
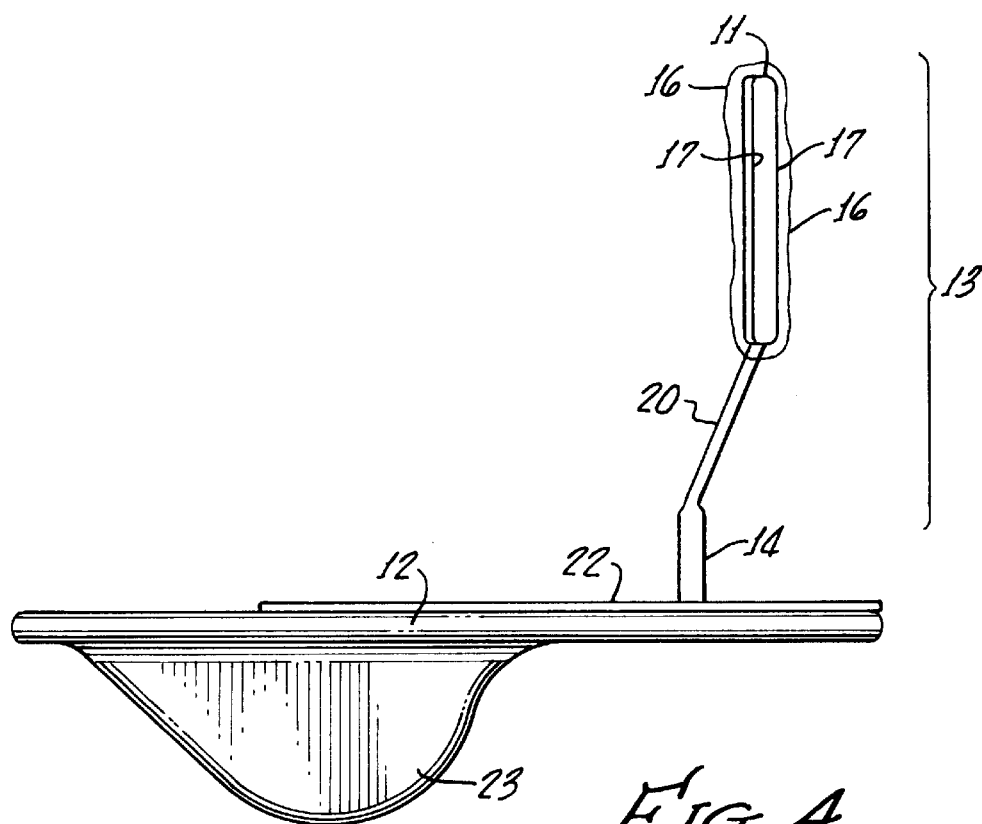
FIG. 4 is a side view shown as an elevation of the female continence augmentor of FIG. 1.
Figure 5:
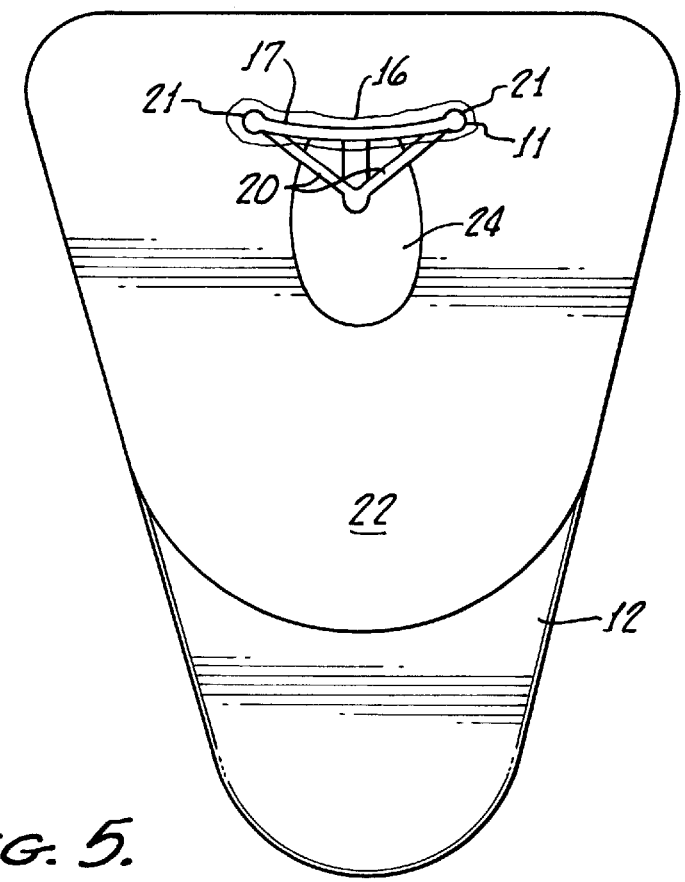
FIG. 5 is top plan view of the female continence augmentor of FIG. 1.
Figure 6:
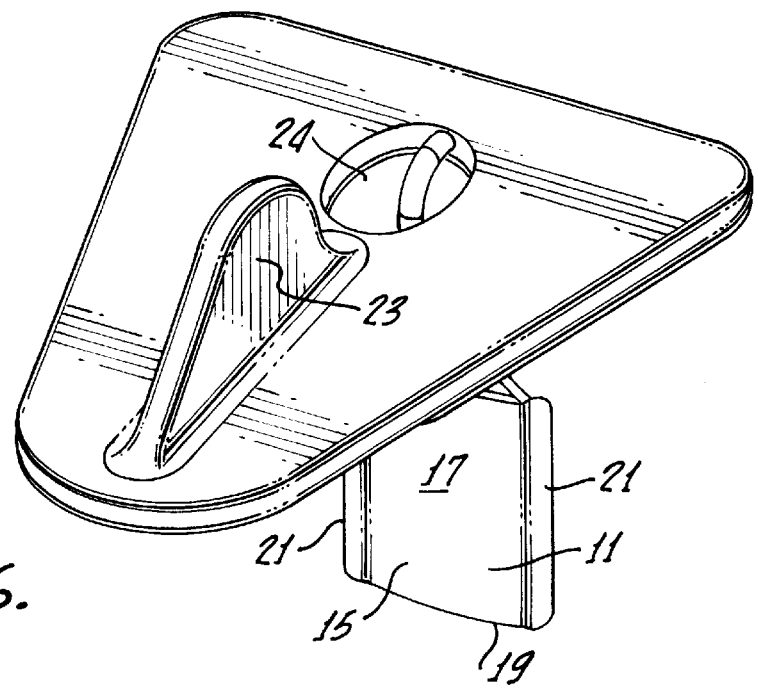
FIG. 6 is a bottom view in perspective of the female continence augmentor of FIG. 1.

The flexible membrane 11, 11' or 11" or the member 15, 15' or 15" is preferably arcuate or bowed for added resilience along the edge 19, 19' or 19" transverse to the opposite sides 21, 21' or 21" for forming the flexible membrane 11,11' or 11" to bear against the midurethral walls. The flexible membrane 11,11' or 11" may be formed of a mesh as shown in FIG. 3. The opposed major surfaces 17, 17' or 17" might perhaps be concave and convex generally in accord with the contour of the midurethral lumen cross section.

The mount 12, 12', 12" or 12"' includes a layer of adhesive 22, 22' or 22" applied thereto and the adhesive is adapted to releasably attach to the female body. The adhesive 22, 22', 22" or 22"' is biocompatible and resistant to perspiration and body oils. FIGS. 2, 3, 4 and 6 show a handle 23 for use in removal of the female incontinence augmentor 10, 10', 10". Similarly, handle 23 could be added to the other embodiments. In FIGS. 1, 2, 5, 6, 7, 8, 10, 11, 12, 14, 15, 16 and 19 an opening 24 is shown to permit the flow of urine during voiding.

A method of making the female continence augmentor 10, 10', 10" or 10"' adapted to prevent involuntary urine loss and improve urethral coaptation by increasing mid-urethral resistance to opening the lumen. The method of making has the steps of forming the mount 12, 12', 12" or 12"' of resilient material including the resilient portion 14, 14 or 14" carried thereon for extending into but not blocking the urethra for at least urging the dorsal midurethral wall in a dorsal direction toward the vagina for stretching and/or reshaping the midurethral lumen to have a more arcuate shape transversely thereacross. The method of making has the steps of connecting the intralumenal part 13, 13', 13" or 13"' to the mount 12, 12', 12" or 12"' and locating the one or more struts 20 for supporting the flexible membrane 11, 11' or 11" or the member 15, 15' or 15". The method has the step of extending the one or more struts 20 from the resilient portion 14, 14' or 14" in position for placement and support of the flexible membrane 11, 11' or 11" or the member 15, 15' or 15" intralumenally. The method of making includes the step of molding the mount 12, 12', 12" or 12"' of a polymer material. The method of making has the step of locating two struts 20 in the midurethral lumen. The method of making has the steps of adding adhesive 22, 22', 22" or 22"' to the mount 12,12', 12" or 12"' and having biocompatible material 16, 16' or 16" on the member 15, 15' or 15" to improve coaptation.

A method of using the female continence augmentor 10, 10', 10" or 10"' with its mount 12, 12', 12" or 12"' connected to intralumenal part 13, 13', 13" or 13"'. The method of using includes the steps of inserting the intralumenal part 13, 13', 13" or 13"' into the urethra so that the flexible membrane 11, 11' or 11", the member 15, 15' or 15" or the two struts 20 thereon are within the midurethral lumen. The step of placing the mount 12, 12', 12" or 12"' adjacent to the urethral exit to retain the member 15, 15' or 15" in the midurethral lumen can be performed. Stretching and/or reshaping the inside of the urethra with the flexible membrane 11, 11' or 11", the member 15, 15' or 15" or the two struts 20 by their connection with resilient portion 14, 14', 14" or 14"' that is connected between the mount 12, 12', 12" or 12"' and member 15, 15' or 15" is a step. The method of using includes steps of urging the dorsal midurethral wall in a dorsal direction for stretching and/or reshaping the midurethral lumen to have a more arcuate shape transversely thereacross. The step of engaging the urethral wall, especially the midurethral wall to remove laxity therein enhances coaptation and increases urethral resistance to opening. The patient may void voluntarily without requiring conscious action to operate the female continence augmentor 10, 10', 10" or 10"' so there is no need to remove, activate, inactivate, alter, it. Following voiding, the female continence augmentor 10, 10', 10" or 10"' resumes functioning automatically.

Figure 20:
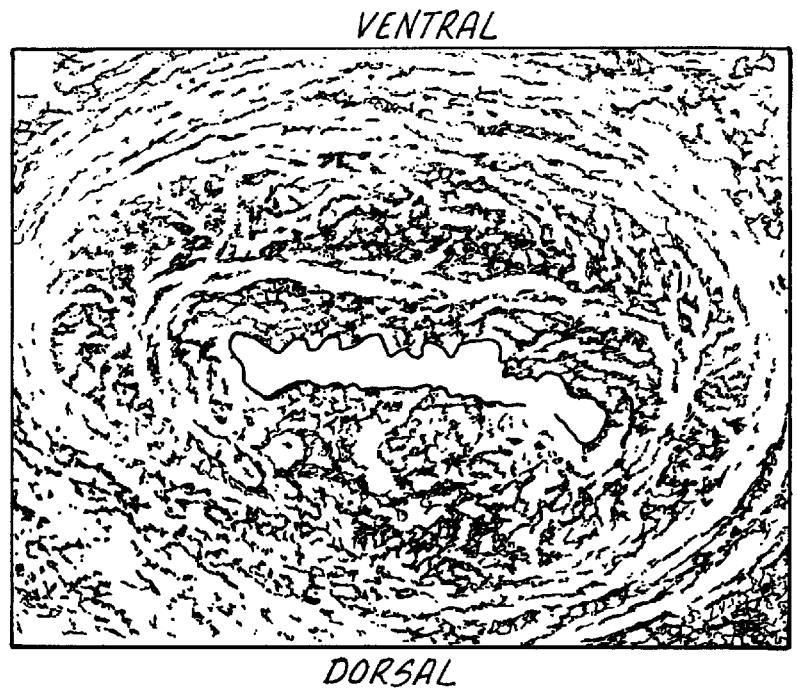
FIG. 20 is a view shown in cross section through the midurethral lumen of a female.
Figure 21:
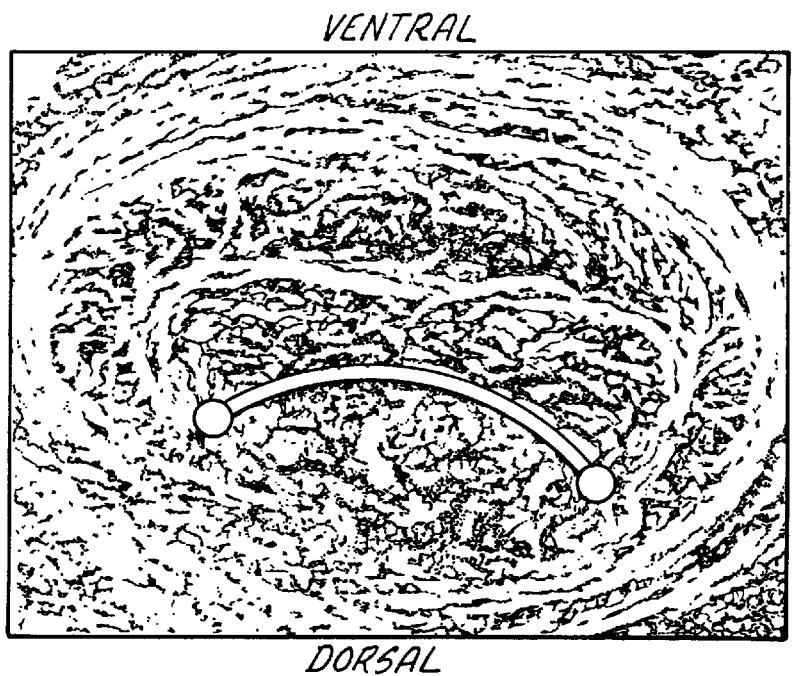
FIG. 21 is a view in cross section through the midurethral lumen of a female and is similar to the view in FIG. 20 however the female continence augmenter is shown in situ.

FIG. 20 is a view shown in cross section through the urethral lumen of a female. Note the irregular arcuate passage of the urethral lumen. FIG. 21 is a view in cross section through the urethral lumen of a female and is similar to the view in FIG. 20 however the female continence augmentor is shown in situ. Note that in FIG. 21 the laxity of the urethral lumen has been alleviated by the incontinence augmentor 10, 10', 10" or 10"'. While a preferred embodiment and alternatives have been shown and described, the female continence augmentor 10, 10', 10" or 10"' sought to be protected by the claims that follow stretches and/or reshapes the midurethral lumen cross section.

What is claimed is:

1. A female continence augmentor adapted to prevent involuntary urine loss due to transient increases in bladder pressure but to passively allow urine flow upon voluntary emptying of the bladder, the female continence augmentor for improving urethral coaptation while increasing mid-urethral resistance to opening the lumen, the female continence augmentor comprising:

a mount formed of a resilient material, the mount adapted to adhere to the female body and support the female continence augmentor in position to prevent inadvertent urine loss through the midurethral lumen;

an intralumenal part carried on the mount, the intralumenal part for extending from the mount and into the urethral lumen at least to the midurethra, and a resilient portion carried on the intralumenal part, the resilient portion located intralumenally within the midurethra and adapted to at least urge the dorsal midurethral wall in a dorsal direction to stretch and/or reshape the midurethral lumen to have a more arcuate shape transversely thereacross.

2. The female continence augmentor of claim 1 wherein two struts are included on the resilient portion carried on the intralumenal part, the two struts angled relative to the intralumenal part for urging the midurethral lumen in a dorsal direction, the two struts spaced apart from one another to stretch and/or reshape the midurethral lumen to have a more arcuate shape transversely thereacross, the two struts closer to one another near the intralumenal part resilient portion and spread apart in the midurethral lumen.

3. The female continence augmentor of claim 2 wherein a member is carried on two or at least one of the struts, the member shaped for positioning intralumenally and for engaging the urethral wall, especially the midurethral wall to remove laxity therein and for enhancing coaptation and increasing urethral resistance to opening so the female may void voluntarily without requiring conscious action to operate the female continence augmentor or needing to remove, activate, inactivate, alter, it and following voiding, the female continence augmentor to resume functioning automatically.

4. The female continence augmentor of claim 1 wherein the mount includes a layer of adhesive applied thereto and adapted to releasably attach to the female body.

5. The female continence augmentor of claim 3 wherein the member is a flexible membrane of thin polymeric material, the flexible membrane may have major surfaces of the member with interstices thereacross, the membrane is surrounded by an edge.

6. The female continence augmentor of claim 5 wherein the opposed major surfaces are generally rectangular and two struts extend from opposite sides of the edge to the intralumenal part so that the flexible membrane may be urged by the two struts against the dorsal wall of the mid urethral lumen.

7. The female continence augmentor of claim 5 wherein the major surfaces are opposed and generally rectangular and the two struts extend from opposite sides of the edge to the intralumenal part resilient portion and wherein the upper and lower edges of the flexible membrane are beveled to provide smooth transitions and enhance the continuity of coaptation along the edges.

8. The female continence augmentor of claim 6 wherein the member includes a coaptation improver located in position for and adapted to engage with the adjacent midurethral walls, the coaptation improver carrying biocompatible hydrophilic material adapted to coact with mucus and mucosa within the urethra to prevent involuntary urine loss.

9. The female continence augmentor of claim 6 wherein the flexible membrane is coated across at least its opposed major surfaces with the biocompatible hydrophilic material which cooperatively fills between the midurethral walls and the flexible membrane to promote adherence therebetween to seal and prevent involuntary urine loss thereacross.

10. The female continence augmentor of claim 6 wherein the flexible membrane is bowed along the edge transverse to the sides for forming the flexible membrane into a resilient but arcuate structure bearing against the midurethral walls.

11. The female continence augmentor of claim 6 wherein the flexible membrane is formed of a mesh of flexible polymer.

12. The female continence augmentor of claim 5 wherein the member has an arcuate shape between the opposite sides wherein the opposed major surfaces are concave and convex generally in accord with the contour of the midurethral lumen cross section.

13. A female continence augmentor to prevent involuntary urine loss due to transient increases in bladder pressure but to passively allow urine flow upon voluntary bladder emptying, the female continence augmentor for improving urethral coaptation while increasing mid-urethral resistance to opening the lumen, the female continence augmentor comprising:

a mount formed of a resilient material, the mount adapted to adhere to the female body and support the female continence augmentor in position to prevent inadvertent urine loss through the midurethral lumen, the mount including a layer of adhesive applied thereto and adapted to releasably attach to the female body;

an intralumenal part carried on the mount, the intralumenal part for extending from the mount and into the urethral lumen at least to the midurethra;

a resilient portion carried on the intralumenal part, the resilient portion located intralumenally and within the midurethra, the resilient portion adapted to at least urge the dorsal midurethral wall in a dorsal direction to stretch and/or reshape the midurethral lumen to have a more arcuate shape transversely thereacross;

two struts on the resilient portion carried on the intralumenal part, the two struts angled relative the intralumenal part for urging the midurethral lumen in a dorsal direction, the two struts spaced apart from one another to stretch and/or reshape the midurethral lumen to have a more arcuate shape transversely thereacross, the two struts closer to one another near the intralumenal part and spread apart in the midurethral lumen.

14. The female continence augmentor of claim 13 wherein a member extends between the two struts.

15. The female continence augmentor of claim 13 wherein a flexible membrane extends between the two struts, the flexible membrane having opposed major surfaces that are generally rectangular, and an edge circumscribing the flexible membrane so the membrane has opposite sides and is bowed along the edge transverse to the sides for forming the flexible membrane into structure bearing against the inside of the midurethral walls, the flexible membrane is formed of a mesh of flexible polymer, and a coaptation improver on the flexible membrane and coated across at least its opposed major surfaces with the biocompatible hydrophilic material to promote coaptation with the inside of the urethra to seal and prevent involuntary urine loss, the coaptation improver carried for positioning and adapted for engagement with the adjacent midurethral walls, the biocompatible hydrophilic material adapted to coact with mucus and mucosa within the urethra to prevent involuntary urine loss.

16. A method of making a female continence augmentor adapted to prevent involuntary urine loss and for improving urethral coaptation and increasing mid-urethral resistance to opening the lumen, the method having the steps of:

forming a mount of a resilient material;

supporting the female continence augmentor extending from the mount for extending into an urethra intralumenal position to prevent inadvertent urine loss through the midurethral lumen, and including a resilient portion carried on the mount for extending into the urethra for urging the dorsal midurethral wall in a dorsal direction for stretching and/or reshaping the midurethral lumen to have a more arcuate shape transversely thereacross;

supporting two struts on the resilient portion in position for placement relative to the resilient portion intralumenally with the two struts located and adapted for engaging the urethral wall, especially the midurethral wall for removing laxity therein and for enhancing coaptation and increasing urethral resistance to opening, so the female may void voluntarily without requiring conscious action normal micturition to operate the female continence augmentor and with no need to remove, activate, inactivate, alter, it and following voiding the female continence augmentor to resume functioning automatically.

17. The method of making of claim 16 with the step of forming including molding the mount of a polymer material.

18. The method of making of claim 16 with the step of carrying a member between the two struts between the resilient portion and the member.

19. The method of claim 16 with the steps of adding an adhesive to the mount for adherence to the female and a biocompatible material on the member to enhance coaptation.

20. A method of using a female continence augmentor including a mount connected to an intralumenal part; the method of using with the steps of:

adhering the mount adapted to the female body;

inserting the intralumenal part carrying a member into the urethra so that the member thereon is within the midurethral lumen;

placing the mount adjacent to the urethral exit to retain the member in the midurethral lumen;

stretching and/or reshaping the inside of the urethra with the member;

urging with the member the dorsal midurethral wall in a dorsal direction for stretching and/or reshaping the midurethral lumen to have a more arcuate shape transversely thereacross, and engaging the urethral wall, especially the midurethral wall with the member to remove laxity therein and for enhancing coaptation and increasing urethral resistance to opening so the female may void voluntarily without requiring conscious action to operate the female continence augmentor or with no need to remove, activate, inactivate, alter, it and following voiding the female continence augmentor to resume functioning automatically.

* * * * *